(12) United States Patent
Hamase et al.

(10) Patent No.: US 10,753,911 B2
(45) Date of Patent: Aug. 25, 2020

(54) CHIRAL ANALYSIS METHOD OF BOUND AMINO ACID AND CHIRAL ANALYSIS SYSTEM

(71) Applicant: KAGAMI INC., Osaka (JP)

(72) Inventors: Kenji Hamase, Fukuoka (JP); Shoto Ishigo, Fukuoka (JP); Yurika Miyoshi, Fukuoka (JP); Tadashi Ueda, Fukuoka (JP); Masashi Mita, Tokyo (JP)

(73) Assignee: KAGAMI INC., Osaka (JP)

( * ) Notice: Subject to any disclaimer, the term of this patent is extended or adjusted under 35 U.S.C. 154(b) by 222 days.

(21) Appl. No.: 15/555,862

(22) PCT Filed: May 10, 2016

(86) PCT No.: PCT/JP2016/063835
§ 371 (c)(1),
(2) Date: Sep. 5, 2017

(87) PCT Pub. No.: WO2016/181956
PCT Pub. Date: Nov. 17, 2016

(65) Prior Publication Data
US 2018/0045690 A1  Feb. 15, 2018

(30) Foreign Application Priority Data
May 11, 2015  (JP) ................. 2015-096959

(51) Int. Cl.
*G01N 30/06* (2006.01)
*G01N 30/88* (2006.01)
(Continued)

(52) U.S. Cl.
CPC ............. *G01N 30/06* (2013.01); *G01N 30/74* (2013.01); *G01N 30/78* (2013.01); *G01N 30/88* (2013.01); *G01N 33/68* (2013.01); *G01N 30/7233* (2013.01); *G01N 30/8679* (2013.01); *G01N 2030/067* (2013.01); *G01N 2030/8818* (2013.01); *G01N 2030/8877* (2013.01); *G01N 2560/00* (2013.01)

(58) Field of Classification Search
None
See application file for complete search history.

(56) References Cited

U.S. PATENT DOCUMENTS 6,040,133 A  3/2000  Kent et al.
7,601,542 B2  10/2009  Emmett et al.

OTHER PUBLICATIONS

T. Miyamoto, M. Sekine, T. Ogawa, M. Hidaka, H. Homma, H. Masaki, "Generation of Enantiomeric Amino Acids during Acid Hydrolysis of Peptides Detected by the Liquid Chromatography / Tandem Mass Spectroscopy" Chemistry & Biodiversity—vol. 7(2010), pp. 1644 to 1649.

(Continued)

*Primary Examiner* — Xiaoyun R Xu
(74) *Attorney, Agent, or Firm* — IPUSA, PLLC

(57) ABSTRACT

A chiral analysis method of a bound amino acid includes a step of hydrolyzing a bound amino acid using a deuterium chloride-deuterium oxide solution and/or deuterium oxide; a step of separating, by chiral separation, a D-form and an L-form of an amino acid generated by the hydrolyzation; a step of generating fragments from the separated amino acid; and a step of selecting and analyzing a predetermined fragment that contains an α carbon and does not contain a side chain from the generated fragments, by mass spectrometry.

14 Claims, 2 Drawing Sheets

(51) Int. Cl.
G01N 30/74 (2006.01)
G01N 30/78 (2006.01)
G01N 33/68 (2006.01)
G01N 30/86 (2006.01)
G01N 30/72 (2006.01)

(56) References Cited

OTHER PUBLICATIONS

Tetsuya Miyamoto, "Tanpakushitsu ni Fukumareru D-Amino Acid Zanki no Kenshutsu ni Kansuru Kenkyu", Hakushi Ronbun (Oyo Seimei Kogaku Senko), The University of Tokyo (online), Mar. 24, 2011, pp. 76 to 139, with English concise explanation.
International Search Report for PCT/JP2016/063835 dated Aug. 9, 2016.
Christopher M. Adams et al: "Distinguishing and Quantifying Peptides and Proteins Containing D-Amino Acids by Tandem Mass Spectrometry" Analytical Chemistry, vol. 77, No. 14, Jul. 15, 2005, pp. 4571-4580, XP055524815.
Extended European Search Report for 16792681.5 dated Nov. 28, 2018.

CHIRAL ANALYSIS METHOD OF BOUND AMINO ACID AND CHIRAL ANALYSIS SYSTEM

BACKGROUND OF THE INVENTION

1. Field of the Invention

The present invention relates to a chiral analysis method of a bound amino acid and a chiral analysis system of a bound amino acid.

2. Description of the Related Art

Bound amino acids are a compound in which amino acids are bonded by amide bonds (peptides bonds) to form a chain, exist as a protein or a peptide in an organism, and are important components as same as sugars, lipids and the like. An α-amino acid in which an amino group is bonded to α carbon (α carbon) to which a carboxyl group is bonded, except a glycine, is a chiral molecule for which optical isomers of a D-form (D-isomer) and an L-form (L-isomer) each containing the α carbon as an optical center exist. Most of the bound amino acids exist in an organism are constituted by L-amino acids, and it has been considered that D-amino acids which are optical isomers thereof are extremely limited biomolecules such as constituents of peptidoglycans or the like that exist in the cell wall of a bacteria.

However, recently, in accordance with progresses of chiral analysis techniques capable of distinguishing the D-amino acid and the L-amino acid, it has been revealed that various D-amino acids exist in mammals in addition to microorganisms or plants, and the D-amino acids can affect physiological phenomenon.

Identification and quantification of amino acid residues of bound amino acids such as a protein are performed using separation techniques such as chromatography or the like for amino acids generated by hydrolysis generally using heat or an acid. However, there is a risk that artifacts may be generated due to isomerization by which the D-form and the L-form interchange with each other in this process, and the artifacts become obstacles in an accurate analysis of originally contained chiral molecules.

Non-Patent Document 1 discloses a chiral analysis method of calculating a ratio of D-forms and L-forms of amino acid residues (% D:D/(D+L)) using an LC/ESI-MS/MS including a chiral column after hydrolyzing a protein using deuterium chloride. At this time, as an hydrogen atom bonded to an α carbon is substituted by a deuterium atom in an amino acid that is isomerized during the hydrolysis process, the amino acid that is isomerized during the hydrolysis process is differentiated from an amino acid that is not isomerized based on a difference in mass-to-charge ratios by mass spectrometry of ions containing α carbons.

NON-PATENT DOCUMENT

[non-Patent Document 1] T. Miyamoto, M. Sekine, T. Ogawa, M. Hidaka, $H_2$. Homma, H. Masaki: Generation of Enantiomeric Amino Acids during Acid Hydrolysis of Peptides Detected by the Liquid Chromatography/Tandem Mass Spectroscopy, Chem. Biodivers., 7, 1644-1649 (2010).

However, according to the method described in non-Patent Document 1, there is a possibility, for an amino acid residue that contains a side chain, that a hydrogen atom contained in the side chain is also substituted by a deuterium atom. In such a case, it is impossible to differentiate an artifact in which the hydrogen atom contained in the side chain is substituted by the deuterium atom from an artifact in which the hydrogen atom bonded to the α carbon is substituted by the deuterium atom, by mass spectrometry. Thus, there is a problem that an accuracy is greatly reduced in the chiral analysis of amino acid residues that are originally included in bound amino acids with a very small amount.

SUMMARY OF THE INVENTION

Thus, an embodiment of the invention is made in light of the above problems, and provides a chiral analysis method of bound amino acids and a chiral analysis system, by which an artifact generated during an analysis process of the bound amino acids, and a D-amino acid residue and/or an L-amino acid residue originally included in the bound amino acids can be very accurately distinguished.

According to an embodiment, there is provided a chiral analysis method of a bound amino acid including a step of hydrolyzing a bound amino acid using a deuterium chloride-deuterium oxide solution and/or deuterium oxide; a step of separating, by chiral separation, a D-form and an L-form of an amino acid generated by the hydrolyzation; a step of generating fragments from the separated amino acid; and a step of selecting and analyzing a predetermined fragment that contains an α carbon and does not contain a side chain from the generated fragments, by mass spectrometry.

According to an embodiment, there is provided a chiral analysis system of a bound amino acid including an chiral separation part that separates, by chiral separation, a D-form and an L-form of an amino acid generated by hydrolyzing the bound amino acid using a deuterium chloride-deuterium oxide solution and/or deuterium oxide; a fragment generation part that generates fragments from the separated amino acid; and a mass spectrometry part that selects and analyzes a predetermined fragment that contains an α carbon and does not contain a side chain from the generated fragments, by mass spectrometry.

According to the present invention, a chiral analysis method of bound amino acids and a chiral analysis system are provided, by which an artifact generated during an analysis process of the bound amino acids, and a D-amino acid residue and/or an L-amino acid residue originally included in the bound amino acids can be very accurately distinguished.

DETAILED DESCRIPTION OF THE PREFERRED EMBODIMENTS

Figure 1:
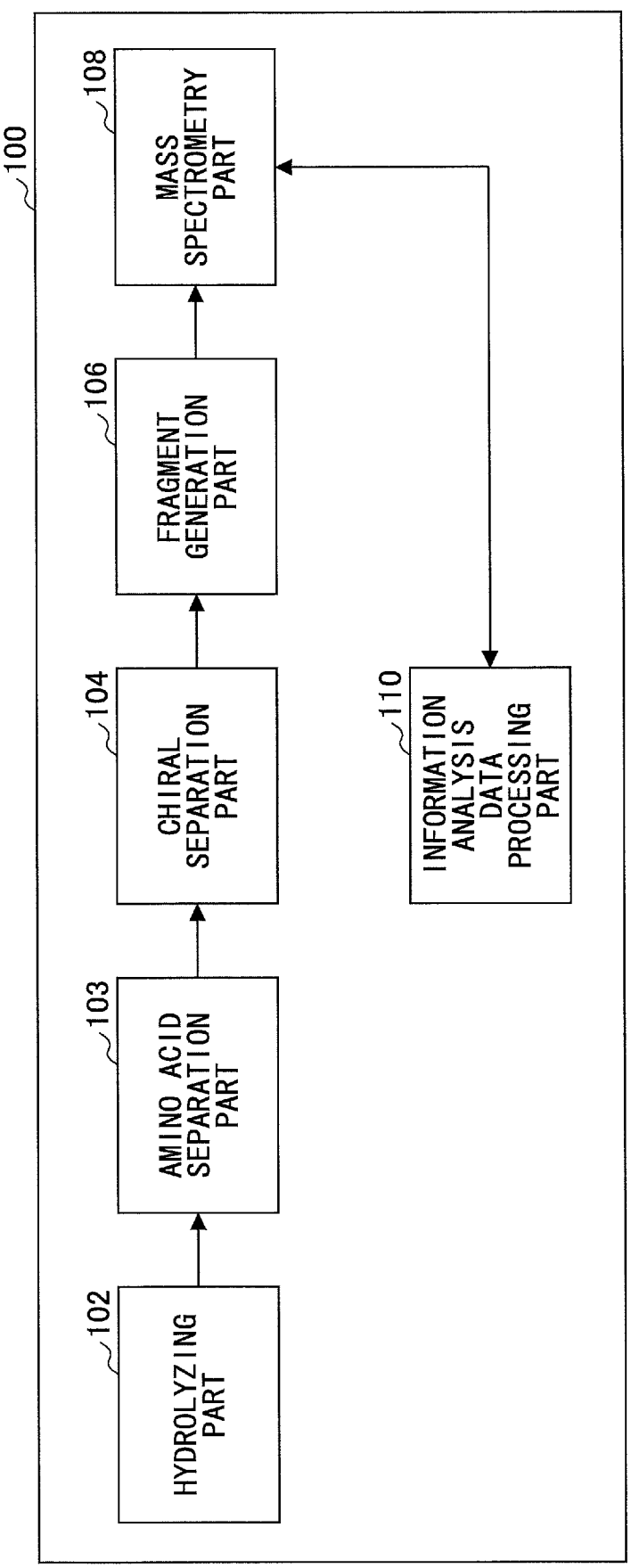
FIG. 1 is a view illustrating an example of a structure of a chiral analysis system of bound amino acids of an embodiment.

Next, embodiments of the present invention are described with reference to drawings.

A chiral analysis method of bound amino acids of the embodiment includes a step of hydrolyzing bound amino acids using a deuterium chloride-deuterium oxide solution and/or deuterium oxide (heavy water), a step of separating, by chiral separation, a D-form and an L-form of an amino acid generated by the hydrolyzation, a step of generating fragments from the separated amino acid, and a step of selecting and analyzing a predetermined fragment that contains an α carbon and does not contain a side chain from the generated fragments, by mass spectrometry.

According to the chiral analysis method of the bound amino acids of the embodiment, an artifact generated during an analysis process of the bound amino acids, and a D-amino acid residue and/or an L-amino acid residue originally included in the bound amino acids can be very accurately distinguished.

The bound amino acids are compounds in which amino acids are bonded by amide bonds (peptides bonds) to form a chain, and exist as a protein or a peptide in an organism, for example.

The hydrolyzation of the bound amino acids is, generally, a reaction in which water reacts with the bound amino acids, and free amino acids are obtained as decomposition products.

In the step of hydrolyzing the bound amino acids, conventional hydrolysis methods may be applied using a deuterium chloride-deuterium oxide solution, deuterium oxide or the like. For example, the hydrolysis method described in non-Patent Document 1 may be used.

Here, hydrolysis conditions such as temperature, concentration of deuterium chloride or deuterium oxide and period may be selectably set. Here, the free amino acids obtained by such hydrolyzation may include amino acids that maintain steric configurations of the bound amino acid residues, respectively, and amino acids that are isomerized during the process.

As an example, a free aspartic acid obtained by hydrolyzing the bound amino acids by reacting with deuterium is described.

First, an aspartic acid residue originally included in the bound amino acids is illustrated in chemical formula (1).

[Chem. 1]

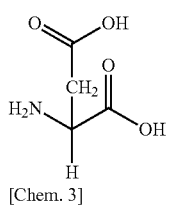

(1)

Next, aspartic acids that are obtained by hydrolyzing the bound amino acids and that are not isomerized in the process are illustrated in chemical formulas (2) to (4).

[Chem. 2]

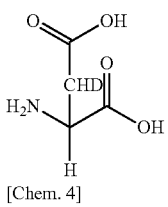

(2)

[Chem. 3]

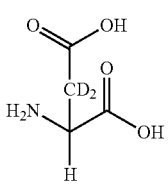

(3)

[Chem. 4]

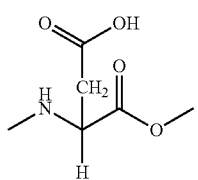

(4)

Further, aspartic acids that are obtained by hydrolyzing the bound amino acids and that are isomerized during the process are illustrated in chemical formulas (5) to (7).

[Chem. 5]

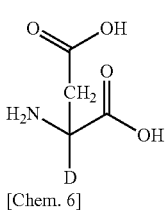

(5)

[Chem. 6]

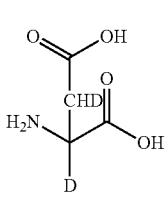

(6)

[Chem. 7]

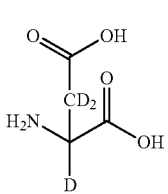

(7)

Next, the D-form and the L-form of the amino acid obtained by hydrolyzing the bound amino acids are separated, by chiral separation.

The method of separating, by chiral separation, the L-form and the L-form of the amino acid is not specifically limited, but methods using a difference in properties of crystallization, optical rotation or an enzyme reaction, a diastereoisomer method, a method using a phase distribution in which asymmetric elements are different or the like may be considered suitable. Among them, a chromatography method that uses a stationary phase (column) having a chiral identifying capability is preferable.

For an amino acid residue containing a side chain containing a hydrogen atom that can be substituted by a deuterium atom, such as the above described aspartic acid, for example, as one hydrogen is substituted by deuterium per molecule in each of the structures of chemical formula (3) and chemical formula (5), the resulting compounds would have the same weight. Similarly, as two hydrogens are substituted by deuterium, respectively, per molecule in each of the structures of chemical formula (4) and chemical formula (6), the resulting compounds would have the same weight. For such molecules having such structures, although the history of isomerization in the process is different, it is impossible to separate (distinguish) them based on the weight.

In this embodiment, further, fragments are generated for each of the separated amino acids or amino acid derivatives by fragmentation. Here, by the fragmentation, one or more fragments each of whose weight is less than that of the amino acid or the amino acid derivative before the fragmentation can be generated.

These fragments may be generated by heat, pressure, molecular collision or the like for each of the separated D-form and L-form, and for example, may be generated by using a molecular collision mechanism provided in a mass spectrometer.

As an example, in aspartic acid, for example, a fragment that contains an α carbon and does not contain a side chain as illustrated in chemical formula (8) is generated. Further, at this time, a fragment that contains an α carbon and/or a side chain may also be generated.

[Chem. 8]

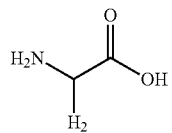

(8)

Next, the generated fragments are separated and detected by mass spectrometry to select and analyze a predetermined fragment that contains an α carbon and does not contain a side-chain. Specifically, it is possible to distinguished, among predetermined fragments each containing an α carbon and does not contain a side-chain, a fragment whose hydrogen atom bonded to an α carbon is substituted by a deuterium atom from a fragment whose hydrogen atom bonded to an α carbon is not substituted by a deuterium atom. Next, based on the information, one that retains a steric configuration of the bound amino acid residue and one that is isomerized during the process are identified, respectively, and an abundance ratio of D-amino acids and L-amino acids or amounts of the D-amino acids and the L-amino acids can be analyzed.

As such, even for an amino acid residue containing a side chain containing a hydrogen atom that can be substituted by a deuterium atom, by generating, separating, detecting, selecting and analyzing a predetermined fragment that contains an α carbon and does not contain a side-chain, an artifact in which a deuterium atom is introduced in a side chain can be removed With this, an artifact generated during an analysis process of the bound amino acids, and a D-amino acid residue and/or an L-amino acid residue originally included in the bound amino acids can be very accurately distinguished.

Here, a structure of each of the fragments can be estimated by analyzing, for example, a mass spectrum of a standard product in which a target amino acid is substituted by an isotope.

In the chiral analysis method of the bound amino acids, in order to improve efficiencies of the chiral separation or the mass spectrometry, amino acids may be derivatized before the chiral separation of the D-forms and the L-forms of the amino acids, or after the chiral separation of the D-forms and the L-forms of the amino acids.

A derivatization regent used for derivatizing the amino acids is not specifically limited, but 4-Fluoro-7-nitrobenzofurazan, 4-Fluoro-7-nitro-2,1,3-benzoxadiazole, o-Phthalaldehyde, Isothiocyanic Acid Phenyl Ester, Fluorescamine, 5-(Dimethylamino)naphthalene-1-sulfonyl Chloride (Dansyl Chloride) or the like may be considered suitable.

The chiral analysis method of the bound amino acids of the embodiment is preferably used in analyzing and distinguishing (identifying) a D-form and an L-form of amino acid residues present in the bound amino acids and each containing a side chain containing a hydrogen atom that can be substituted by a deuterium atom in a hydrolysis step. In such a case, the D-forms and the L-forms of all of the amino acid residues contained in the bound amino acids may be analyzed using the chiral analysis method of the bound amino acids of the embodiment, or the D-forms and the L-forms of only the amino acid residues each containing a side chain containing a hydrogen atom that can be substituted by a deuterium atom.

A group containing a hydrogen atom that can be substituted by a deuterium atom is not specifically limited, but may be a methylene group or the like. For example, a methylene group or the like that is bonded to an electron-withdrawing group such as a carboxyl group may be used.

An amino acid containing a methylene group bonded to a carboxyl group is not specifically limited, but may include aspartic acid (Asp), glutamic acid (Glu) or the like.

Here, the chiral analysis method of the bound amino acids of the embodiment may also be applied to artificially synthesized bound amino acids in addition to naturally existing bound amino acids.

FIG. 1 is a view illustrating an example of a structure of a chiral analysis system 100 of bound amino acids of the embodiment. The chiral analysis system 100 of the bound amino acids of the embodiment includes an chiral separation part 104 that separates, by chiral separation, a D-form and an L-form of an amino acid generated by hydrolyzing the bound amino acids using a deuterium chloride-deuterium oxide solution and/or deuterium oxide, a fragment generation part 106 that generates a fragment that contains an α carbon and does not contain a side chain for each of the separated amino acid, and a mass spectrometry part 108 that detects the generated fragment by mass spectrometry.

Here, the chiral analysis system 100 of the bound amino acids may further include a hydrolyzing part 102 that hydrolyzes the bound amino acids by reacting with deuterium oxide. Further, the chiral analysis system 100 of the bound amino acids may further include an amino acid separation part 103 that separates amino acids hydrolyzed at the hydrolyzing part 102 when the bound amino acids contain plural kinds of amino acids. Further, the chiral analysis system 100 of the bound amino acids may further include an information analysis data processing part that analyzes detected information in the mass spectrometry part 108, or not only in the mass spectrometry part 108, or may include an information analysis data processing part 110 that analyzes the detected information separately.

The hydrolyzing part 102 is, for example, a thermostatic reaction oven capable of drying a sample including the bound amino acids and retaining it under a vacuumed state, and includes a mechanism that hydrolyzes the bound amino acids. However, the hydrolyzing part 102 may not be incorporated in the chiral analysis system 100 as a specific device and may be a structure that performs the hydrolysis process off-line.

The amino acid separation part 103 includes, for example, a reversed-phase micro column or the like, and separates a target amino acid from other components. The amino acid separation part 103 may be integrally configured with the chiral separation part 104.

The chiral separation part 104 includes, for example, a chromatographic separation mechanism using a stationary phase that can identify optical activities of the sample after the hydrolyzation.

The fragment generation part 106 includes, for example, a mechanism that fragments the separated sample, by the chiral separation, by applying energy such as molecular collision.

The mass spectrometry part 108 includes, for example, a mechanism that ionizes the sample, separates and detects fragment ions by an electric action, a magnetic action or the like in accordance with mass-to-charge ratios, and obtains a mass spectrum regarding a mass-to-charge ratio and a detection intensity.

The information analysis data processing part 110 includes, for example, a mechanism that selects a target fragment ion from the mass spectrum, performs a qualitative analysis or a quantitative analysis, and outputs measured data, ratio data or the like, for example. The configuration of the information analysis data processing part 110 may be embodied by any appropriate combination of hardware and software, typified by a CPU of a suitable computer, a memory, a program loaded in the memory, a storage unit for storing the program such as a hard disk, and an interface for network connection.

According to the chiral analysis system 100 of the bound amino acids configured as such, an artifact generated during an analysis process of the bound amino acids, and a D-amino acid residue and/or an L-amino acid residue originally included in the bound amino acids can be very accurately distinguished.

Example

After adding 250 µL of 0.1M deuterium chloride (produced by ACROS ORGANICS) whose D content was 100% to 1 mg of a peptide ($H_2N$—)Gly-Pro-Glu-Ala-Asp-Ser-Gly (—COOH) (produced by WATANABE CHEMICAL INDUSTRIES, LTD.) synthesized by amino acids of only L-forms, as the bound amino acids, and leaving still at 4° C. for one night, water was evaporated to be dried. Further, after adding 200 µL of 6M deuterium chloride (produced by ACROS ORGANICS) whose D content was 100%, and hydrolyzing at 110° C. for 20 hours using a heater (produced by Waters), water was evaporated to be dried. Next, after adding 100 µL of water, and filtering by a filter (produced by Millipore) having a pore size of 0.45 µm, the sample was centrifuged at 8000 rpm for 5 minutes to obtain 100 µL of free amino acid aqueous solution.

After adding 10 µL of 400 mM sodium borate buffer solution whose pH was 8.0, and 5 µL of 40 mM acetonitrile solution of NBD-F (4-Fluoro-7-nitrobenzofurazan) (produced by Tokyo Chemical Industry Co., Ltd.) to 10 µL of the obtained free amino acid aqueous solution, and reacting at 60° C. for two minutes, 75 µL of 2 volume % trifluoroacetate aqueous solution was added to terminate the reaction, and NBD derivatives of the amino acids were obtained.

The NBD derivatives of the amino acids were analyzed using a two-dimensional HPLC-FL-MS/MS system. At this time, apparatus structures and analysis conditions of the two-dimensional HPLC-FL-MS/MS system were as follows. Here, the NBD derivative of each of the amino acids was separated using a first dimensional column in the amino acid separation part 103. Further, a D-form and an L-form of each of the amino acids were separated using a second dimensional column in the chiral separation part 104.

Apparatus Structures
(First Dimensional)
Liquid supplying pump: 3301 (produced by Shiseido Co., Ltd.)
Column oven: 3004 (produced by Shiseido Co., Ltd.)
Auto-sampler: 3033 (produced by Shiseido Co., Ltd.)
Fluorescence detector: 3213 (produced by Shiseido Co., Ltd.)
Data processing program: Ezchrome Elite (produced by Shiseido Co., Ltd.)
(Second Dimensional)
Liquid supplying pump: 3201 (produced by Shiseido Co., Ltd.)
Degasser: 3202 (produced by Shiseido Co., Ltd.)
Column oven: 3014 (produced by Shiseido Co., Ltd.)
Auto-sampler: 3033 (produced by Shiseido Co., Ltd.)
High-pressure valve: 3011 (produced by Shiseido Co., Ltd.)
Fluorescence detector: 3013 (produced by Shiseido Co., Ltd.)
Mass spectrometer: TQ-5500 (produced by produced by AB Sciex)
Data processing program: Analyst (produced by AB Sciex)
Analysis Conditions
(First Dimensional)
Column: monolithic ODS column (0.53 mm (inner diameter)×1000 mm)
Mobile phase: 0 to 35 min; A 100%, 35 to 55 min; A 100% to B 100% (gradient), 55 to 100 min; B 100%, 100 to 130 min; C 100%, 130 to 180 min; A 100%
Flow rate of mobile phase: 25 µL/min
A: 5 mass % acetonitrile, 0.05 mass % trifluoroacetate aqueous solution
B: 18 mass % acetonitrile, 0.05 mass % trifluoroacetate aqueous solution
C: 85 mass % acetonitrile aqueous solution
(Second Dimensional)
Column: Sumichiral OA-3200S (1.5 mm (inner diameter)×250 mm)
Mobile phase for glutamic acid: acetonitrile/methanol (volume ratio: 80/20) solution of 0.8 mass % formic acid
Mobile phase for aspartic acid: acetonitrile/methanol (volume ratio: 50/50) solution of 1 mass % formic acid
Flow rate of mobile phase: 150 µL/min
Fluorescence detector: fluorescence intensity was measured at an excitation wavelength of 470 nm and a fluorescent wavelength of 530 nm
Mass spectrometer: fragment ions obtained by applying collision energies of 37 eV (Asp); 21 eV (Glu) to parent ions (m/z: 299 (Asp); 313 (Glu)) generated at ionization voltage of 5500 V, temperature of 600° C. were measured.

The mass spectrometer corresponds to the fragment generation part 106 and the mass spectrometry part 108.

As fragment ions detected by the mass spectrometry, (1) an ion containing an α carbon and a side chain derived from the NBD derivative of the aspartic acid (m/z: 192) (Asp, with side chain), (2) an ion containing an α carbon but does not contain a side chain derived from the NBD derivative of the aspartic acid (m/z: 237) (Asp, without side chain),
(3) an ion containing an α carbon and a side chain derived from the NBD derivative of the glutamic acid (m/z: 247) (Glu, with side chain), and
(4) an ion containing an α carbon but does not contain a side chain derived from the NBD derivative of the glutamic acid (m/z: 149) (Glu, without side chain) were selected.

Here, (1) and (3) target fragments in each of which a hydrogen atom bonded to the α carbon is not substituted by a deuterium atom.

Figure 2:
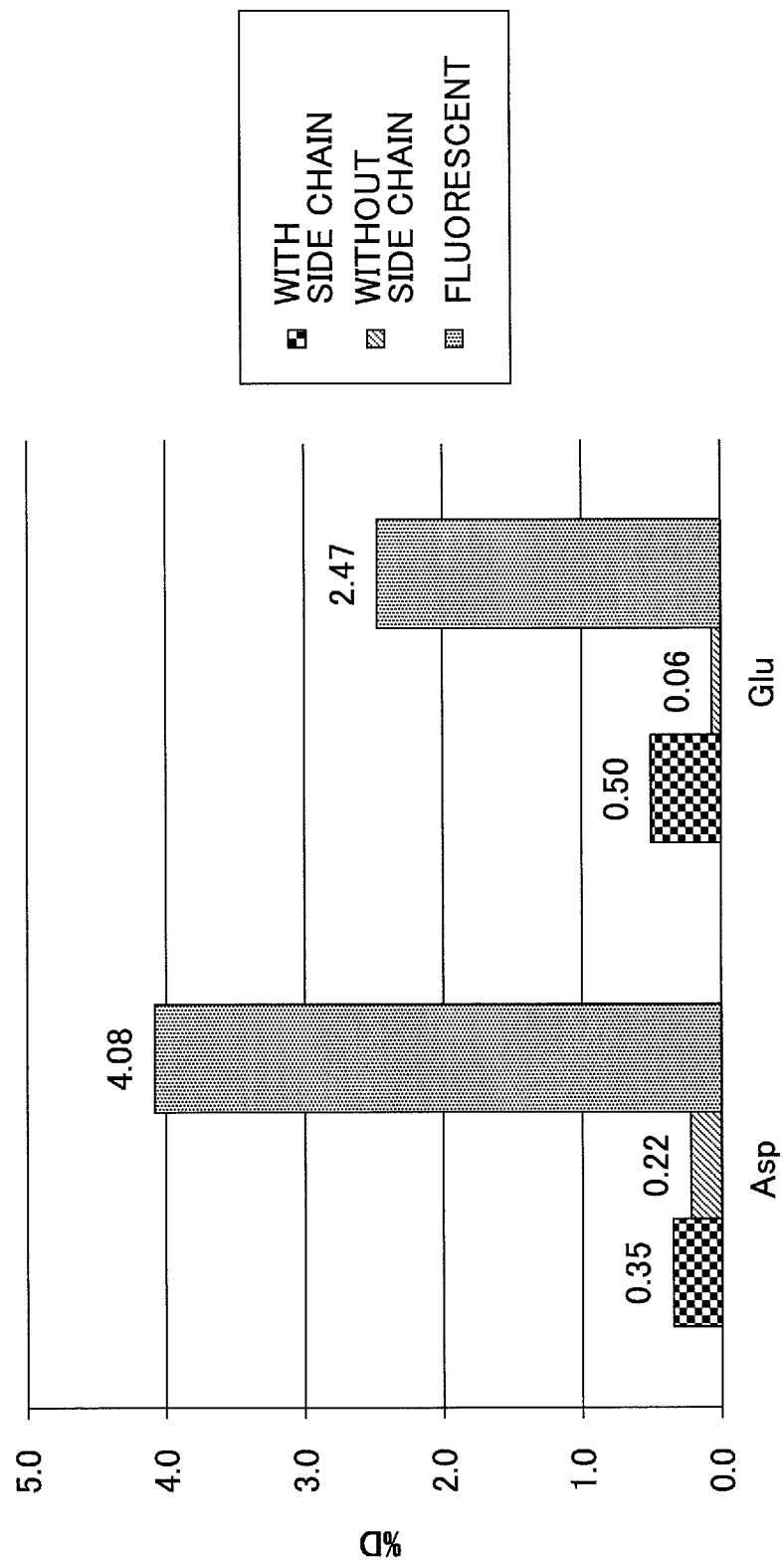
FIG. 2 is a view illustrating a result of a chiral analysis of aspartic acid and glutamic acid included in a hydrolysis product of a peptide.

FIG. 2 illustrates a result of a chiral analysis of the aspartic acid and the glutamic acid contained in the hydrolysis product of the peptide. In FIG. 2, in addition to results of above (1) to (4), fluorescent detection results are also illustrated.

Here, % D was calculated from a chromatogram of fluorescent or MS, by a formula (height of a peak of a D-form in the chromatogram)/(height of a peak of a D-form of a standard product in the chromatogram)/{(height of a peak of an L-form in the chromatogram)/(height of a peak of an L-form of the standard product in the chromatogram)+(height of the peak of the D-form in the chromatogram)/(height of the peak of the D-form of the standard product in the chromatogram)}×100.

It can be understood from FIG. 2 that even though the peptide synthesized by the amino acids of only L-forms was used, D-forms were also detected. These are estimated as artifacts that are generated because the hydrogen atom bonded to the α carbon was not substituted by the deuterium atom during the isomerizing reaction due to purity of the reagent, bound water of the protein, protons included in the deuterium chloride or the sample used in the sample reaction. However, as can be understood from FIG. 2, for a fragment ion that contains an α carbon and does not contain a side chain derived from the NBD derivative of the aspartic acid (Asp, without side chain), the detection amount of the D-form is lowered compared with a fragment ion that contains a side chain derived from the NBD derivative of the aspartic acid (Asp, with side chain) or a fluorescent detection result. When detection sensitivities are compared by calculating detection limits by a signal/noise ratio (S/N), for the fragment ion that contains an α carbon and does not contain a side chain derived from the NBD derivative of the aspartic acid, the detection sensitivity is improved 18.5 times compared with the fluorescent detection, which does not have an identifying or selecting capability for the artifacts, and improved 1.6 times compared with the fragment ion that contains the side chain.

Further, for a fragment ion that contains an α carbon and does not contain a side chain derived from the NBD derivative of the glutamic acid (Glu, without side chain), the detection amount of the D-form is lower in comparison with a fragment ion that contains a side chain derived from the NBD derivative of the glutamic acid (Glu, with side chain) or a fluorescent detection result. When detection sensitivities are compared by calculating detection limits by a signal/noise ratio (S/N), for the fragment ion that contains an α carbon and does not contain a side chain derived from the NBD derivative of the glutamic acid, the detection sensitivity is improved 41.2 times in comparison with the fluorescent detection, and improved 8.3 times in comparison with the fragment ion that contains the side chain.

These results indicate that an artifact generated during the analysis process, and a D-amino acid residue and/or an L-amino acid residue originally included in the bound amino acids can be very accurately distinguished by selecting a fragment ion that contains an α carbon and does not contain a side chain as a fragment ion to be detected.

Although the preferred embodiments and examples are described in detail, the present invention is not limited to the specifically disclosed embodiments, and numerous variations and modifications may be made without departing from the spirit and scope of the present invention.

The present application is based on and claims the benefit of priority of Japanese Priority Application No. 2015-096959 filed on May 11, 2015, the entire contents of which are hereby incorporated by reference.

What is claimed is:

1. A chiral analysis method of a bound amino acid comprising:
    a step of hydrolyzing a bound amino acid using a deuterium chloride-deuterium oxide solution and/or deuterium oxide;
    a step of separating, by chiral separation, a D-form and an L-form of an amino acid generated by the hydrolyzation;
    a step of generating fragments from the separated amino acid; and
    a step of selecting and analyzing a predetermined fragment that contains an α carbon and does not contain a side chain from the generated fragments, by mass spectrometry.

2. The chiral analysis method of the bound amino acid according to claim 1, wherein the D-form and the L-form of the amino acid generated by the hydrolyzation are separated by the chiral separation through a chromatographic method.

3. The chiral analysis method of the bound amino acid according to claim 1, further comprising:
    a step of derivatizing the amino acid generated by the hydrolyzation,
    wherein the D-form and the L-form of the derivatized amino acid are separated by the chiral separation.

4. The chiral analysis method of the bound amino acid according to claim 1,
    wherein in the step of generating the fragments, the fragments are generated for each of the separated D-form and the L-form of the amino acid, and
    wherein in the step of analyzing, the predetermined fragment that contains the α carbon and does not contain the side chain is selected for each of the separated D-form and the L-form of the amino acid, and an abundance ratio of the D-form or the L-form of the amino acid originally included in the bound amino acid is analyzed based on the predetermined fragment of the D-form and the predetermined fragment of the L-form.

5. The chiral analysis method of the bound amino acid according to claim 4, wherein in the step of analyzing, the predetermined fragment is a fragment that contains the α carbon and does not contain the side chain, a hydrogen atom bonded to the α carbon being not substituted by a deuterium atom.

6. The chiral analysis method of the bound amino acid according to claim 1, wherein in the step of generating the fragments, the fragments are generated from the amino acid by heat, pressure or molecular collision.

7. A chiral analysis system of a bound amino acid comprising:
    an chiral separation part that separates, by chiral separation, a D-form and an L-form of an amino acid generated by hydrolyzing the bound amino acid using a deuterium chloride-deuterium oxide solution and/or deuterium oxide;

a fragment generation part that generates fragments from the separated amino acid; and a mass spectrometry part that selects and analyzes a predetermined fragment that contains an α carbon and does not contain a side chain from the generated fragments, by mass spectrometry.

8. The chiral analysis system of the bound amino acid according to claim 7, further comprising:

a hydrolyzing part that hydrolyzes the bound amino acid using a deuterium chloride-deuterium oxide solution and/or deuterium oxide.

9. The chiral analysis system of the bound amino acid according to claim 7, wherein the mass spectrometry part includes an information analysis data processing part that analyzes the detected information.

10. The chiral analysis system of the bound amino acid according to claim 7, further comprising:

an information analysis data processing part that analyzes the detected information.

11. The chiral analysis method of the bound amino acid according to claim 1, wherein in the step of selecting and analyzing the predetermined fragment, a fragment that contains a side chain is not selected and analyzed.

12. The chiral analysis method of the bound amino acid according to claim 1, wherein an amino acid moiety of the predetermined fragment does not contain a side chain.

13. The chiral analysis system of the bound amino acid according to claim 7, wherein the mass spectrometry part does not select or analyze a fragment that contains a side chain.

14. The chiral analysis system of the bound amino acid according to claim 7, wherein an amino acid moiety of the predetermined fragment does not contain a side chain.

* * * * *